(12) United States Patent
Olejnik et al.

(10) Patent No.: US 6,641,834 B2
(45) Date of Patent: *Nov. 4, 2003

(54) COMPOSITIONS CONTAINING ALPHA-2-ADRENERGIC AGONIST COMPONENTS

(75) Inventors: Orest Olejnik, Coto de Coza, CA (US); Edward D. S. Kerslake, Charlestown, MA (US)

(73) Assignee: Allergan Sales, Inc., Irvine, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 10/236,566

(22) Filed: Sep. 6, 2002

(65) Prior Publication Data

US 2003/0027811 A1 Feb. 6, 2003

Related U.S. Application Data

(63) Continuation of application No. 09/904,018, filed on Jul. 10, 2001.
(60) Provisional application No. 60/218,200, filed on Jul. 14, 2002.

(51) Int. Cl.[7] .................... A61K 33/14; A61K 9/00; A61K 9/08
(52) U.S. Cl. ............... 424/427; 424/400; 424/401; 424/466; 424/422; 514/772.4; 514/772.6; 514/249
(58) Field of Search .................. 424/661, 400, 424/427, 401, 422; 514/772.4, 772.6, 249

(56) References Cited

U.S. PATENT DOCUMENTS

| | | | |
|---|---|---|---|
| 3,278,447 A | 10/1966 | McNicholas | |
| 3,890,319 A | 6/1975 | Danielwicz et al. | |
| 4,530,920 A | 7/1985 | Nestor et al. | |
| 4,806,556 A | 2/1989 | Portoghese | |
| 5,021,416 A | 6/1991 | Gluchowski | |
| 5,202,128 A | 4/1993 | Morella et al. | |
| 5,215,991 A * | 6/1993 | Burke | 514/255 |
| 5,352,796 A | 10/1994 | Hoeger et al. | |
| 5,459,133 A | 10/1995 | Neufeld | |
| 5,703,077 A | 12/1997 | Burke et al. | |
| 5,719,197 A | 2/1998 | Kanios et al. | |
| 5,725,887 A | 3/1998 | Martin et al. | |
| 5,814,638 A | 9/1998 | Lee et al. | |
| 5,834,502 A | 11/1998 | Cheng et al. | |
| 5,994,110 A | 11/1999 | Mosbach et al. | |
| 6,358,935 B1 * | 3/2002 | Beck et al. | 514/58 |
| 2002/0032201 A1 * | 3/2002 | Olejnik et al. | 514/249 |
| 2002/0071874 A1 * | 6/2002 | Olejnik et al. | 424/661 |

FOREIGN PATENT DOCUMENTS

| | | |
|---|---|---|
| CA | 2048315 | 2/1992 |
| EP | 0609961 | 8/1994 |
| WO | 94/16685 | 8/1994 |
| WO | 98/47878 | 10/1998 |
| WO | 99/43299 | 9/1999 |
| WO | 99/51273 | 10/1999 |
| WO | 00/12137 | 3/2000 |
| WO | 00/19981 | 4/2000 |

OTHER PUBLICATIONS

U.S. patent application Ser. No. 09/903,962, filed Jul. 10, 2001.

* cited by examiner

Primary Examiner—Thurman K. Page
Assistant Examiner—Rachel M. Bennett
(74) Attorney, Agent, or Firm—Stout, Uxa, Buyan & Mullins, LLP; Frank J. Uxa; Carlos A. Fisher

(57) ABSTRACT

Compositions useful for improving effectiveness of alpha-2-adrenergic agonist components include carrier components, alpha-2-adrenergic agonist components, solubility enhancing components which aid in solubilizing the alpha-2-adrenergic agonist components. In one embodiment, the alpha-2-adrenergic agonist components include alpha-2-adrenergic agonists. In another embodiment, the solubility enhancing components include carboxymethylcellulose.

22 Claims, 1 Drawing Sheet

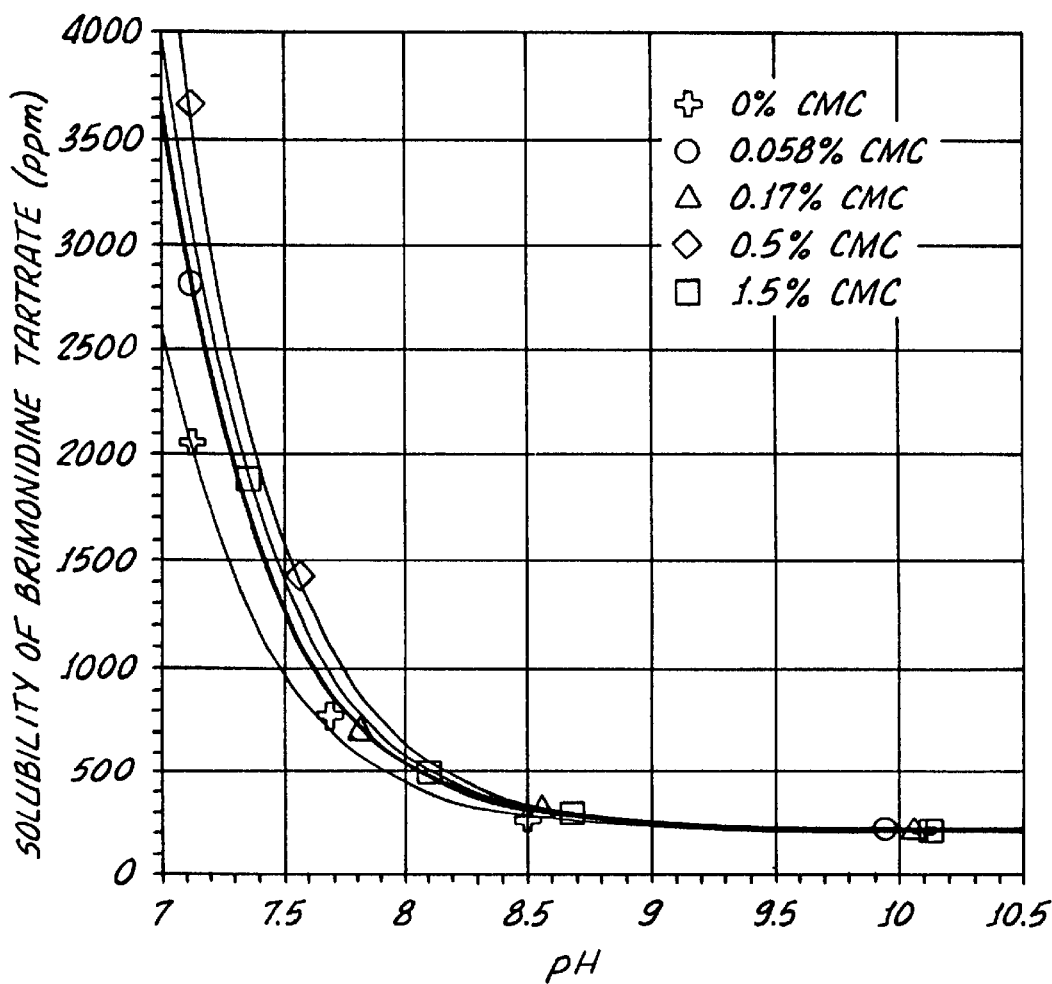

COMPOSITIONS CONTAINING ALPHA-2-ADRENERGIC AGONIST COMPONENTS

CROSS REFERENCE TO RELATED APPLICATION

This application is a continuation of application Ser. No. 09/904,018, filed Jul. 10, 2001 which, in turn, claims the benefit of U.S. Provisional Application Ser. No. 60/218,200, filed Jul. 14, 2000. The disclosure of each of the above-noted applications is incorporated in its entirety herein by reference.

BACKGROUND OF THE INVENTION

The present invention relates to compositions containing alpha-2-adrenergic agonist components. More particularly, the invention relates to such compositions in which the alpha-2-adrenergic agonist components have enhanced solubility at the therapeutically effective concentrations.

Alpha-2-adrenergic agonist components include chemical entities, such as compounds, ions, complexes and the like, which are effective to act on or bind to Alpha-2-adrenergic receptors and provide a therapeutic effect. Alpha-2-adrenergic agonist components means the agonists themselves and any and all precursors thereof, metabolites thereof and combinations thereof. One of the continuing challenges of formulating compositions having alpha-2-adrenergic agonist components is to render such components more effective. For example, alpha-2-adrenergic agonist components in liquid compositions often benefit from being soluble in the liquid carriers of such compositions. Such solubility promotes uniform and accurate administration.

Additionally, the dispensed or administered alpha-2-adrenergic agonist components should advantageously be soluble in biological systems or environments, for example, for effective or enhanced in vivo diffusion through cell membranes or lipid bilayers. Some alpha-2-adrenergic agonist components with higher pKa's, for example, greater than about 7, tend to diffuse very well through lipid membranes at pH valves near their pka, because in such circumstances they are predominantly unionized in neutral to alkaline biological environments. However, some of these alpha-2-adrenergic agonist components become insoluble at neutral to alkaline biological pH's. Such insolubility may decrease membrane diffusion capabilities, rendering the alpha-2-adrenergic agonist components less effective and/or their therapeutic effects more variable at a given dosage. Furthermore, solubilized alpha-2-adrenergic agonist components provide other benefits, for example, reduced irritation to tissues that interact with alpha-2-adrenergic agonist components.

There continues to be a need for new compositions containing alpha-2-adrenergic agonist components.

SUMMARY OF THE INVENTION

New alpha-2-adrenergic agonist component-containing compositions have been discovered. The present compositions contain certain materials which are effective in at least aiding or assisting in solubilizing the alpha-2-adrenergic agonist components in the compositions, and preferably in environments to which the compositions are administered or introduced, for example, biological environments, such as the human eye. Preferably, solubilization of the alpha-2-adrenergic agonist components in accordance with the present invention facilitates transport of such components across lipid membranes. Also, preferably such solubilization allows the provision of more reliable and reproducible dosage forms of the drug. In addition, alpha-2-adrenergic agonist component-containing compositions have been discovered which include preservatives which provide substantial advantages, for example, reduced adverse interactions with the alpha-2-adrenergic agonist components and/or with the patients to whom the compositions are administered, while maintaining preservative effectiveness.

The present compositions preferably enhance the effectiveness of alpha-2-adrenergic agonist components by increasing the apparent water solubility of the alpha-2-adrenergic agonist components, preferably at pH's higher than neutral. The present compositions include, in addition to the adrenergic agonist components, solubility enhancing components (SECs) in amounts effective to enhance the solubility of the alpha-2-adrenergic agonist components. Preferably, the alpha-2-adrenergic agonist components are more soluble in the present compositions having, for example, pH's of about 7 or greater, relative to similar compositions without the SECs. In another embodiment, the alpha-2-adrenergic agonist components of the present compositions are more soluble in neutral, preferably alkaline, biological environments into which the compositions are administered relative to alpha-2-adrenergic agonist components in similar compositions without the SECs.

In one embodiment, the alpha-2-adrenergic agonist components include imino-imidazolines, imidazolines, imidazoles, azepines, thiazines, oxazolines, guanidines, catecholamines, biologically compatible salts and esters and mixtures thereof. Preferably, the alpha-2-adrenergic agonist components include quinoxaline components. Quinoxaline components include quinoxaline, biologically compatible salts thereof, esters thereof, other derivatives thereof and the like, and mixtures thereof. Non-limiting examples of quinoxaline derivatives include (2-imidozolin-2-ylamino) quinoxaline, 5-bromo-6-(2-imidozolin-2-ylamino) quinoxaline, and biologically compatible salts thereof and esters thereof, preferably the tartrate of 5-bromo-6-(2-imidozolin-2-ylamino) quinoxaline, and the like and mixtures thereof. Hereinafter, the tartrate of 5-bromo-6-(2-imidozolin-2-ylamino) quinoxaline is referred to as "Brimonidine tartrate."

In a preferred embodiment, the alpha-2-adrenergic agonist components, such as those listed above, are specific for the alpha-2A-adrenergic receptors, alpha-2B-adrenergic receptors and/or alpha-2D-adrenergic receptors.

In one embodiment, the alpha-2-adrenergic agonist components are unionized in the compositions. Preferably, the alpha-2-adrenergic agonist components are also unionized in the biological environment into which the compositions are administered.

In a useful embodiment, the SEC includes a polyanionic component. As used herein, the term "polyanionic component" refers to a chemical entity, for example, an ionically charged species, such as an ionically charged polymeric material, which includes more than one discrete anionic charge, that is multiple discrete anionic charges. Preferably, the polyanionic component is selected from polymeric materials having multiple anionic charges, and mixtures thereof.

Particularly useful polyanionic components are selected from anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers of amino acids (meaning to include polymers of amino acids, amino acid salts, and the like and mixtures thereof), and the like, and mixtures thereof. Very useful polyanionic components are those selected from anionic cellulose derivatives and mixtures thereof, especially carboxymethylcelluloses.

The polyanionic component preferably is sufficiently anionic to interact with or otherwise affect, in particular increase, the solubility of the alpha-2-adrenergic components. This interaction preferably is sufficient to render the alpha-2-adrenergic components substantially completely soluble at therapeutically effective concentrations. The amount of SEC in the composition preferably is in the range of about 0.1% (w/v) to about 30% (w/v), more preferably about 0.2% (w/v) to about 10% (w/v), and even more preferably about 0.2% (w/v) to about 0.6% (w/v).

The compositions include carrier components, for example, aqueous liquid carrier components. In one embodiment, the compositions have pH's of about 7 or greater, preferably about 7 to about 9, and are ophthalmically acceptable.

In a preferred embodiment, a composition is provided which includes an alpha-2-adrenergic agonist component in an amount effective to provide at least one therapeutic benefit to a patient to whom the composition is administered, an anionic cellulose derivative in an amount effective to increase the solubility of the alpha-2-adrenergic agonist component and an aqueous liquid carrier component. The alpha-2-adrenergic agonist component preferably comprises a tartrate of 5-bromo-6-(2-imidozolin-2-ylamino) quinoxaline. The anionic cellulose derivative preferably comprises a carboxymethylcellulose. The concentration of the anionic cellulose derivative in the composition should be about 0.2% (w/v) to about 0.6% (w/v).

In a preferred embodiment, the present compositions are ophthalmically acceptable, e.g. the compositions do not have deleterious or toxic properties which could harm the eye of the human or animal to whom the compositions are administered.

In one broad aspect of the invention, complexes are formed in the compositions. In one embodiment, the complexes include monomer units derived from at least one quinoxaline component. In a preferred embodiment, the complexes of the present invention are dimers. In a particularly preferred embodiment, the complexes are complexes, especially dimers, of Bromodidine tartrate.

In another broad aspect of the present invention, compositions are provided which comprise an alpha-2-adrenergic agonist component and a preservative component in an effective amount to at least aid in preserving the compositions. Preferably, the preservative components include oxychloro components, such as compounds, ions, complexes and the like which are biologically acceptable, chemically stable and do not substantially or significantly detrimentally affect the an alpha-2-adrenergic agonist component in the compositions or the patients to whom the compositions are administered. Such compositions preferably are substantially free of cyclodextrins in the compositions or the patients to whom the compositions are administered.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE DRAWING

FIG. 1 is a graph of soluble Brimonidine tartrate verses pH at various carboxymethylcellulose concentrations.

DETAILED DESCRIPTION OF THE INVENTION

Compositions comprising alpha-2-adrenergic agonist components and SECs are provided. The alpha-2-adrenergic agonist components in the present compositions are made more soluble and may be more effectively utilized as therapeutic agents. The SECs employed in the present compositions may be effective in the solubilization of ionized alpha-2-adrenergic agonist components, unionized alpha-2-adrenergic agonist components or both. The present compositions include liquid carrier components and have the characteristics of liquid, for example, aqueous liquid, solutions.

Preferably, the alpha-2-adrenergic agonist components have increased solubility in the present compositions at pH's greater than 7, as compared to identical alpha-2-adrenergic agonist components, at comparable concentrations, in similar compositions without the SECs. More preferably, the alpha-2-adrenergic agonist components have increased solubility in the present compositions at pH's in the range of about 7 to about 10 and, as compared to identical alpha-2-adrenergic agonist components in similar compositions, at comparable concentrations, without the SECs.

Without wishing to be limited by any theory or mechanism of operation, it is believed that solubilized alpha-2-adrenergic agonist components are better able to cross the lipid membranes relative to unsolubilized alpha-2-adrenergic agonist components. It is further believed that the solubilized alpha-2-adrenergic agonist components are physically smaller and are therefore more able to physically permeate or diffuse through the lipid membranes.

In one embodiment, the SECs of this invention are capable of solubilizing the alpha-2-adrenergic agonist components in the biological environments into which they are introduced at therapeutically effective concentrations. Preferably, the biological environments into which the present compositions are introduced have pH's ranging from about 7 to about 9. For example, a composition comprising a SEC and an alpha-2-adrenergic agonist component may be administered to the cornea of an eye, which has a pH of about 7, wherein the alpha-2-adrenergic agonist component is substantially solubilized at the administered area. Furthermore, in one embodiment, the alpha-2-adrenergic agonist components solubilized by SECs at the administered area diffuse through biological lipid membranes more readily than alpha-2-adrenergic agonist components which are not solubilized by SECs. The solubilization of alpha-2-adrenergic agonist components preferably reduces irritation to sensitive tissues in contact or interacting with the alpha-2-adrenergic agonist components.

The presently useful alpha-2-adrenergic agonist components preferably are chosen to benefit from the presence of the SECs. In general, the alpha-2-adrenergic agonist components are provided with increased apparent solubility, preferably increased apparent water solubility, by the presence of the SECs.

Examples of alpha-2-adrenergic agonist components include molecules containing amines. Preferably, the alpha- 2-adrenergic agonist components are amine-containing molecules with pKa's of greater than about 7, more preferably about 7 to about 9.

Alpha-2-adrenergic agonist components include alpha-2-adrenergic agonists. As used herein, the term alpha-2 adrenergic agonist includes chemical entities, such as compounds, ions, complexes and the like, that produce a net sympatholytic response, resulting in increased accommodation, for example, by binding to presynaptic alpha-2 receptors on sympathetic postganglionic nerve endings or for example, to postsynaptic alpha-2 receptors on smooth muscle cells. A sympatholytic response is characterized by the inhibition, diminishment, or prevention of the effects of impulses conveyed by the sympathetic nervous system. The alpha-2 adrenergic agonists of the invention bind to the alpha-2 adrenergic receptors presynaptically, causing negative feedback to decrease the release of neuronal norepinephrine. Additionally, they also work on alpha-2 adrenergic receptors postsynaptically, inhibiting beta-adrenergic receptor-stimulated formation of cyclic AMP, which contributes to the relaxation of the ciliary muscle, in addition to the effects of postsynaptic alpha-2 adrenergic receptors on other intracellular pathways. Activity at either pre- or postsynaptic alpha-2 adrenergic receptors will result in a decreased adrenergic influence. Decreased adrenergic influence results in increased contraction resulting from cholinergic innervations. Alpha-2 adrenergic agonists also include compounds that have neuroprotective activity. For example, 5-bromo-6-(2-imidozolin-2-ylamino) quinoxaline is an alpha-2-adrenergic agonist which has a neuroprotective activity through an unknown mechanism.

Without limiting the invention to the specific groups and compounds listed, the following is a list of representative alpha-2 adrenergic agonists useful in this invention: imino-imidazolines, including clonidine, apraclonidine; imidazolines, including naphazoline, xymetazoline, tetrahydrozoline, and tramazoline; imidazoles, including detomidine, medetomidine, and dexmedetomidine; azepines, including B-HT 920 (6-allyl-2-amino-5,6,7,8 tetrahydro-4H-thiazolo[4,5-d]-azepine and B-HT 933; thiazines, including xylazine; oxazolines, including rilmenidine; guanidines, including guanabenz and guanfacine; catecholamines; and the like and derivatives thereof.

Particularly useful alpha-2-adrenergic agonists include quinoxaline components. In one embodiment, the quinoxaline components include quinoxaline, derivatives thereof and mixtures thereof. Preferably, the derivatives of quinoxaline include (2-imidozolin-2-ylamino) quinoxaline. More preferably, the derivatives of quinoxaline include 5-halide-6-(2-imidozolin-2-ylamino) quinoxaline. The "halide" of the 5-halide-6-(2-imidozolin-2-ylamino) quinoxaline may be a fluorine, a chlorine, an iodine, or preferably, a bromine, to form 5-bromo-6-(2-imidozolin-2-ylamino) quinoxaline. Even more preferably, the derivatives of quinoxaline to be used in accordance with this invention include a tartrate of 5-bromo-6-(2-imidozolin-2-ylamino) quinoxaline, or Brimonidine tartrate.

Other useful quinoxaline derivatives are well known. For example, useful derivatives of a quinoxaline include the ones disclose by Burke et al U.S. Pat. No. 5,703,077. See also Danielwicz et al 3,890,319. Each of the disclosures of Burke et al and Danielwicz et al is incorporated in its entirety by reference herein.

The quinoxaline and derivatives thereof, for example Brimonidine tartrate, are amine-containing and preferably have pKa's of greater than 7, preferably about 7.5 to 9.

Analogs of the foregoing compounds that function as alpha-2 adrenergic agonists also are specifically intended to be embraced by the invention.

Preferably, the alpha-2-adrenergic agonists, for example the ones listed above, are effective toward activating alpha-2A-adrenergic receptors, alpha-2B-adrenergic receptors and alpha-2D-adrenergic receptors.

In one embodiment, the alpha-2-adrenergic agonists, for example Brimonidine tartrate, are substantially unionized in the compositions. In another embodiment, the adrenergic compounds are substantially unionized in the environment to which they are administered, for example the cornea. Without wishing to be limited by any theory or mechanism of action, it is believed that the unionized forms of the adrenergic compounds facilitate their permeation across membrane lipid bilayers.

Any suitable SEC may be employed in accordance with the present invention. In one embodiment, the SECs include pyrrolinidone components. Examples of pyrrolinidone components are polyvinylpyrrolinidones and derivatives thereof. In a preferred embodiment, the SECs include polyanionic components. The useful polyanionic components include, but are not limited to, those materials which are effective in increasing the apparent solubility, preferably water solubility, of poorly soluble alpha-2-adrenergic agonist components and/or enhance the stability of the alpha-2-adrenergic agonist components and/or reduce unwanted side effects of the alpha-2-adrenergic agonist components. Furthermore, the polyanionic component is preferably ophthalmically acceptable at the concentrations used. Additionally, the polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the presently useful liquid aqueous media, such as a liquid aqueous medium containing the alpha-2-adrenergic components.

The polyanionic component is preferably sufficiently anionic to interact with the alpha-2-adrenergic agonist component. Such interaction is believed to be desirable to solubilize the alpha-2-adrenergic agonist component and/or to maintain such alpha-2-adrenergic agonist component soluble in the carrier component, for example a liquid medium.

Polyanionic components also include one or more polymeric materials having multiple anionic charges.

Examples include:
metal carboxymethylstarchs
metal carboxymethylhydroxyethylstarchs
hydrolyzed polyacrylamides and polyacrylonitriles
heparin
homopolymers and copolymers of one or more of:
    acrylic and methacrylic acids
    metal acrylates and methacrylates
    alginic acid
    metal alginates
    vinylsulfonic acid
    metal vinylsulfonate
    amino acids, such as aspartic acid, glutamic acid and the like
    metal salts of amino acids
    p-styrenesulfonic acid metal p-styrenesulfonate
2-methacryloyloxyethylsulfonic acids
metal 2-methacryloyloxyethylsulfonates
3-methacryloyloxy-2-hydroxypropylsulonic acids
metal 3-methacryloyloxy-2-hydroxypropylsulfonates
2-acrylamido-2-methylpropanesulfonic acids
metal 2-acrylamido-2-methylpropanesulfonates
allylsulfonic acid
metal allylsulfonate and the like.

In another embodiment, the polyanionic components include anionic polysaccharides which tend to exist in ionized forms at higher pH's, for example, pH's of about 7 or higher. The following are some examples of anionic polysaccharides which may be employed in accordance with this invention.

Polydextrose is a randomly bonded condensation polymer of dextrose which is only partially metabolized by mammals. The polymer can contain a minor amount of bound sorbitol, citric acid, and glucose.

Chondroitin sulfate also known as sodium chondroitin sulfate is a mucopolysaccharide found in every part of human tissue, specifically cartilage, bones, tendons, ligaments, and vascular walls. This polysaccharide has been extracted and purified from the cartilage of sharks.

Carrageenan is a linear polysaccharide having repeating galactose units and 3,6 anhydrogalactose units, both of which can be sulfated or nonsulfated, joined by alternating 1-3 and beta 1-4 glycosidic linkages. Carrageenan is a hydrocolloid which is heat extracted from several species of red seaweed and irish moss.

Maltodextrins are water soluble glucose polymers which are formed by the reaction of starch with an acid and/or enzymes in the presence of water.

Other anionic polysaccharides found useful in the present invention are hydrophilic colloidal materials and include the natural gums such as gellan gum, alginate gums, i.e., the ammonium and alkali metal salts of alginic acid and mixtures thereof. In addition, chitosan, which is the common name for deacetylated chitin is useful. Chitin is a natural product comprising poly-(N-acetyl-D-glucosamine). Gellan gum is produced from the fermentation of pseudomonas elodea to yield an extracellular heteropolysaccharide. The alginates and chitosan are available as dry powders from Protan, Inc., Commack, N.Y. Gellan gum is available from the Kelco Division of Merk & Co., Inc., San Diego, Calif.

Generally, the alginates can be any of the water-soluble alginates including the alkali metal alginates, such as sodium, potassium, lithium, rubidium and cesium salts of alginic acid, as well as the ammonium salt, and the soluble alginates of an organic base such as mono-, di-, or tri- ethanolamine alginates, aniline alginates, and the like. Generally, about 0.2% to about 1% by weight and, preferably, about 0.5% to about 3.0% by weight of gellan, alginate or chitosan ionic polysaccharides, based upon the total weight of the composition, are used to obtain the gel compositions of the invention.

Preferably, the anionic polysaccharides are cyclized. More preferably, the cyclized anionic polysaccharides include less than ten monomer units. Even more preferably, the cyclized polysaccharides include less than six monomer units.

In one embodiment, a particularly useful group of cyclized anionic polysaccharides includes the cyclodextrins. Examples of the cyclodextrin group include, but are not limited to: α-cyclodextrin, derivatives of α-cyclodextrin, β-cyclodextrin, derivatives of β-cyclodextrin, γ-cyclodextrin, derivatives of γ-cyclodextrin, carboxymethyl-β-cyclodextrin, carboxymethyl-ethyl-β-cyclodextrin, diethyl-β-cyclodextrin, dimethyl-β-cyclodextrin, methyl-β-cyclodextrin, random methyl-β-cyclodextrin, glucosyl-β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof. Sulfobutylether-β-cyclodextrin is a preferred cyclized anionic polyasaccharide in accordance with the present invention. It is advantageous that the SEC's, including the above mentioned cyclodextrins, employed in this invention be, at the concentration employed, non-toxic to the mammal, human, to inhibit the present incorporation is administered. As used herein, the term "derivatives" as it relates to a cyclodextrin means any substituted or otherwise modified compound which has the characteristic chemical structure of a cyclodextrin sufficiently to function as a cyclodextrin component, for example, to enhance the solubility and/or stability of active components and/or reduce unwanted side effects of the active components and/or to form inclusive complexes with active components, as described herein.

Although cyclodextrins and/or their derivatives may be employed as SECs, one embodiment of the invention may include SECs other than cyclodextrins and/or their derivatives.

A particularly useful and preferred class of polyanionic component includes anionic cellulose derivatives. Anionic cellulose derivatives include metal carboxymethylcelluloses, metal carboxymethylhydroxyethylcelluloses and hydroxypropylmethylcelluloses and derivatives thereof.

The present polyanionic components often can exist in the unionized state, for example, in the solid state, in combination with a companion or counter ion, in particular a plurality of discrete cations equal in number to the number of discrete anionic charges so that the unionized polyanionic component is electrically neutral. For example, the present unionized polyanionic components may be present in the acid form and/or in combination with one or more metals. Since the polyanionic components are preferably ophthalmically acceptable, it is preferred that the metal associated with the unionized polyanionic component be ophthalmically acceptable in the concentrations used. Particularly useful metals include the alkali metals, for example, sodium and potassium, the alkaline earth metals, for example, calcium and magnesium, and mixtures thereof. Sodium is very useful to provide the counter ion in the unionized polyanionic component. Polyanionic components which, in the unionized states, are combined with cations other than $H^+$ and metal cations can be employed in the present invention.

The amount of SEC in the present compositions is not of critical importance so long as solubility at the alpha-2-adrenergic agonist component is at least somewhat increased and is present in a biologically acceptable amount. Such amount should be effective to perform the desired function or functions in the present composition and/or after administration to the human or animal. In one embodiment, the amount of SEC, preferably the polyanionic component, is sufficient to complex at least in a major amount, and more preferably substantially all, of the alpha-2-adrenergic agonist component in the present composition. In one useful embodiment, the amount of polyanionic component in the present composition is in the range of about 0.1% to about 30% (w/v) or more of the composition. Preferably, the amount of polyanionic component is in the range of about 0.2% (w/v) to about 10% (w/v). More preferably, the amount of polyanionic component is in the range of about 0.2%

(w/v) to about 0.6% (w/v). Even more preferably, the polyanionic component is carboxymethylcellulose and is present in the composition in the range of about 0.2% (w/v) to about 0.6% (w/v). A particularly useful concentration of carboxymethylcellulose in the present compositions is about 0.5%.

In one embodiment, the SECs, for example a carboxymethylcellulose, assist in solubilizing the alpha-2-adrenergic agonist components in the compositions. Although the SECs are capable aiding in the solubilization of ionized alpha-2-adrenergic agonist components, it is preferable that the SECs used in this invention could assist in the solubilization of unionized alpha-2-adrenergic agonist components. For example, in one embodiment, carboxymethylcellulose may help solubilize ionized alpha-2-adrenergic agonist components. In another embodiment, carboxymethylcellulose may help solubilize unionized alpha-2-adrenergic agonist components. In a preferred embodiment, the carboxylmethylcellulose helps solubilize ionized Brimonidine tartrate in the compositions. More preferably, the carboxylmethylcellulose helps solubilize unionized Brimonidine tartrate in the compositions.

In one embodiment, the compositions may also include preservative components or components which assist in the preservation of the composition. The preservative components selected so as to be effective and efficacious as preservatives in the present compositions, that is in the presence of polyanionic components, and preferably have reduced toxicity and more preferably substantially no toxicity when the compositions are administered to a human or animal.

Preservatives or components which assist in the preservation of the composition which are commonly used in pharmaceutical compositions are often less effective when used in the presence of solubilizing agents. In certain instances, this reduced preservative efficacy can be compensated for by using increased amounts of the preservative. However, where sensitive or delicate body tissue is involved, this approach may not be available since the preservative itself may cause some adverse reaction or sensitivity in the human or animal, to whom the composition is administered.

Preferably, the present preservative components or components which assist in the preservation of the composition, preferably the alpha-2-adrenergic agonist components therein, are effective in concentrations of less than about 1% (w/v) or about 0.8% (w/v) and may be 500 ppm (w/v) or less, for example, in the range of about 10 ppm(w/v) or less to about 200 ppm(w/v). Preservative components in accordance with the present invention preferably include, but are not limited to, those which form complexes with the polyanionic component to a lesser extent than does benzalkonium chloride.

Very useful examples of the present preservative components include, but are not limited to oxidative preservative components, for example oxy-chloro components, peroxides, persalts, peracids, and the like, and mixtures thereof. Specific examples of oxy-chloro components useful as preservatives in accordance with the present invention include hypochlorite components, for example hypochlorites; chlorate components, for example chlorates; perchlorate components, for example perchlorates; and chlorite components. Examples of chlorite components include stabilized chlorine dioxide (SCD), metal chlorites, such as alkali metal and alkaline earth metal chlorites, and the like and mixtures therefor. Technical grade (or USP grade) sodium chlorite is a very useful preservative component.

The exact chemical composition of many chlorite components, for example, SCD, is not completely understood. The manufacture or production of certain chlorite components is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purite T by Allergan, Inc. Other examples of oxidative preservative components includes peroxy components. For example, trace amounts of peroxy components stabilized with a hydrogen peroxide stabilizer, such as diethylene triamine penta(methylene phosphonic acid) or 1-hydroxyethylidene-1,1-diphosphonic acid, may be utilized as a preservative for use in components designed to be used in the ocular environment. Also, virtually any peroxy component may be used so long as it is hydrolyzed in water to produce hydrogen peroxide. Examples of such sources of hydrogen peroxide, which provide an effective resultant amount of hydrogen peroxide, include sodium perborate decahydrate, sodium peroxide and urea peroxide. It has been found that peracetic acid, an organic peroxy compound, may not be stabilized utilizing the present system. See, for example, Martin et al U.S. Pat. No. 5,725,887, the disclosure of which is incorporated in its entirety herein by reference.

Preservatives other than oxidative preservative components may be included in the compositions. The choice of preservatives may depend on the route of administration. Preservatives suitable for compositions to be administered by one route may possess detrimental properties which preclude their administration by another route. For nasal and ophthalmic compositions, preferred preservatives include quaternary ammonium compounds, in particular the mixture of alkyl benzyl dimethyl ammonium compounds and the like known generically as "benzalkonium chloride." For compositions to be administered by inhalation, however, the preferred preservative is chlorbutol and the like. Other preservatives which may be used, especially for compositions to be administered rectally, include alkyl esters of p-hydroxybenzoic acid and mixtures thereof, such as the mixture of methyl, ethyl, propyl, butyl esters and the like which is sold under the trade name "Nipastat."

In another broad aspect of the present invention, compositions are provided which comprise an alpha-2-adrenergic agonist component, a preservative component in an effective amount to at least aid in preserving, preferably in an amount effective to preserve, the compositions and a liquid carrier component. Preferably, the preservative components include oxy-chloro components, such as compounds, ions, complexes and the like which (1) do not substantially or significantly detrimentally affect the alpha-2-adrenergic agonist components in the compositions or the patients to whom the compositions are administered, and (2) are substantially biologically acceptable and chemically stable. Such compositions in accordance with the present invention comprise an alpha-2-adrenergic agonist component, an oxy-chloro component, and a liquid carrier component, and preferably are substantially free of cyclodextrins.

The carrier components useful in the present invention are selected to be non-toxic and have no substantial detrimental effect on the present compositions, on the use of the compositions or on the human or animal to whom the compositions are administered. In one embodiment, the carrier component is a liquid carrier. In a preferred embodiment, the carrier component is a liquid aqueous carrier component. A particularly useful aqueous liquid carrier component is that derived from saline, for example, a conventional saline solution or a conventional buffered saline solution. The aqueous liquid carrier preferably has a pH in the range of about 6 to about 9 or about 10, more preferably about 6 to about 8, and still more preferably about 7.5. The liquid medium preferably has an ophthalmically acceptable tonicity level, for example, of at least about 200 mOsmol/kg, more preferably in the range of about 200 to about 400 mOsmol/kg. In an especially useful embodiment, the osmolality or tonicity of the carrier component substantially corresponds to the tonicity of the fluids of the eye, in particular the human eye.

In one embodiment, the carrier components containing the SECs and the alpha-2-adrenergic agonist components may have viscosities of more than about 0.01 centipoise (cps) at 25° C., preferably more than about 1 cps at 25° C., even more preferably more than about 10 cps at 25° C. In a preferred embodiment, the composition has a viscosity of about 50 cps at 25° C. and comprises a conventional buffer saline solution, a carboxymethylcellulose and a Brimonidine tartrate.

In order to insure that the pH of the aqueous liquid carrier component, and thus the pH of the composition, is maintained within the desired range, the aqueous liquid carrier component may include at least one buffer component. Although any suitable buffer component may be employed, it is preferred to select such component so as not to produce a significant amount of chlorine dioxide or evolve significant amounts of gas, such as $CO_2$. It is preferred that the buffer component be inorganic. Alkali metal and alkaline earth metal buffer components are advantageously used in the present invention.

Any suitable ophthalmically acceptable tonicity component or components may be employed, provided that such component or components are compatible with the other ingredients of the liquid aqueous carrier component and do not have deleterious or toxic properties which could harm the human or animal to whom the present compositions are administered. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The present compositions may conveniently be presented as solutions or suspensions in aqueous liquids or non-aqueous liquids, or as oil-in-water or water-in-oil liquid emulsions. The present compositions may include one or more additional ingredients such as diluents, flavoring agents, surface active agents, thickeners, lubricants, and the like, for example, such additional ingredients which are conventionally employed in compositions of the same general type.

The present compositions in the form of aqueous suspensions may include excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gun tragacanth and gun acacia; dispersing or wetting agents may be a naturally occurring phosphatide, for example, lecithin, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof. Such aqueous suspensions may also contain one or more coloring agents, one or more flavoring agents and one or more sweetening agents, such as sucrose, saccharin, and the like and mixtures thereof.

The present compositions in the form of oily suspensions may be formulated in a vegetable oil, for example, olive oil, sesame oil or coconut oil, or in a mineral oil such as liquid paraffin. Such suspensions may contain a thickening agent, for example beeswax, hard paraffin or cetyl alcohol. Sweetening agents, such as those set forth above, and flavoring agents may be added to provide a palatable oral preparation.

The present compositions may also be in the form of oil-in-water emulsions. The oily phase may be a vegetable oil, for example, olive oil or arachis oil, or a mineral oil, for example, liquid paraffin, and the like and mixtures thereof. Suitable emulsifying agents may be naturally-occurring gums, for example, gum acacia or gun tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate. The emulsions may also contain sweetening and flavoring agents.

The present compositions in the form of syrups and elixirs may be formulated with sweetening agents, for example, as described elsewhere herein. Such formulations may also contain a demulcent, and flavoring and coloring agents.

The specific dose level for any particular human or animal depends upon a variety of factors including the activity of the active component employed, the age, body weight, general health, sex, diet, time of administration, route of administration, rate of excretion, drug combination and the severity of the particular condition undergoing therapy.

In one broad aspect of the invention, complexes are formed in the present compositions. In one embodiment, the complexes include at least one monomer unit of a quinoxaline component. Examples of quinoxaline components include quinoxaline, (2-imidozolin-2-ylamino) quinoxaline, 5-bromo-6-(2-imidozolin-2-ylamino) quinoxaline, salts thereof, esters thereof, other derivatives thereof, and the like and mixtures thereof. For example, in one embodiment, a complex of the present invention may include a conjugation of 5-bromo-6-(2-imidozolin-2-ylamino) quinoxaline monomer units. In another embodiment, the complex may include a conjugation of 5-bromo-6-(2-imidozolin-2-ylamino) quinoxaline monomer units and Brimonidine tartrate monomer units.

In a preferred embodiment, the complexes of the present invention are dimers. For example, a dimer in accordance with the present invention may include a quinoxaline and a 5-bromo-6-(2-imidozolin-2-ylamino) quinoxaline. Preferably, a dimer in accordance with the present invention includes two Brimonidine tartrate monomer units.

Without wishing to limit the invention to any theory or mechanism of operation, it is believed that any peroxide forming agent or strong oxidizing agent such as the oxidative preservative components, for example oxy-chloro components, peroxides, persalts, peracids, and the like, and mixtures thereof may facilitate the formation of the complexes, preferably complexes of alpha-2-adrenergic agonist components. For example, dimers of Brimonidine tartrate monomer units are believed to be formed in the presence of chlorites, preferably stabilized chlorine dioxide.

Furthermore, it is believed that the interactions between the monomers which serve to hold the monomers or monomer subunits together to form a complex, preferably an oligomer and more preferably a dimer, may include, but not limited to, covalent bonding, ionic bonding, hydrophobic bonding, electrostatic bonding, hydrogen bonding, other chemical and/or physical interactions, and the like and combinations thereof. Such complexes may disassociate in liquid, for example, aqueous liquid, media. In one embodiment, the monomers or monomer subunits are held together by other than covalent bonding. In one embodiment, the monomers or monomer subunits are held together by electrostatic bonding or forces.

The following non-limiting examples illustrate certain aspects of the present invention.

EXAMPLE 1

Brimonidine tartrate has a pKa of about 7.78. The pH-solubility profile of 0.5% (w/v) Brimonidine tartrate in a formulation, Ophthalmic Solution, was established in the pH range of about 5 to about 8 at 23° C. Table 1. It will be understood that concentrations of adrenergic agonists other than 0.5% may be used, so long as they have therapeutic activity. Likewise, the temperature may be varied, for example, solubility curves may be performed at 37° C. (98.6° F.). The formulation vehicle was prepared by first dissolving polyvinyl alcohol (PVA) in water. The PVA was added to approximately ⅓ of the required total amount of purified water with constant stirring. The slurry was stirred for 20–30 minutes and then heated to 80–95° C. with constant stirring. The mixture was removed from the heat source within 1 hour after having reached the temperature of 80–90° C. and stirred for an additional 10 minutes to ensure homogeneity (Part I). The other ingredients of the Ophthalmic Solution, except for Brimonidine tartrate, were dissolved in a separate container with an additional ⅓ of the required total amount of purified water (Part II). The PVA mixture (Part I) was then quantitatively transferred to Part II using several rinse volumes of purified water. The solution was adjusted to final volume with purified water without pH adjustment.

Brimonidine tartrate was weighed and transferred to a 10 mL test tube containing 5 mL of the formulation vehicle described above. The pH of each sample was then adjusted to a desired value using dilute sodium hydroxide and/or dilute hydrochloric acid. The samples were placed in a rack on a stir plate and stirred at high speed to achieve uniform mixing for 2 days; a partition was placed between the rack and the stir plate to prevent any heat diffusion from the stir plate to the samples. The temperature of the laboratory was monitored throughout the study and was found to be 23±1° C.

At the end of two days of stirring, the pH value of each sample was measured, and then approximately 1 mL of each sample was placed in a micro centrifuge tube (polypropylene) and centrifuged at 4,000 rpm for 10 minutes. The supernatant was filtered through a 1 μm filter unit (Whatman, 13 mm, PTFE). The first 3–4 drops of the filtrate were discarded; the rest of the filtrate was received and diluted quantitatively with HPLC mobile phase. The dilute sample was then injected directly on the HPLC column (Dupont Zorbax, 250 mm×4.6 mm, 5 μm) for Brimonidine tartrate assay in order to quantify the amount of Brimonidine tartrate. A control of 10.05% Brimonidine tartrate was prepared in the formulation vehicle at pH 6.3–6.5 and assayed before (untreated) and after (treated) centrifugation and filtration. This was done to evaluate the potential loss of Brimonidine tartrate in these two steps of the sample preparation. To ensure reproducibility, the study was repeated on consecutive days.

TABLE I

| 0.5% Brimonidine tartrate in Ophthalmic Solution. | |
|---|---|
| Ingredient | Percent (w/v) |
| Brimonidine tartrate | 0.50 |
| Benzalkonium Chloride, NF | 0.0050 |
| Polyvinyl Alcohol, USP | 1.4 |
| Sodium Chloride, USP | 0.66 |
| Sodium Citrate, Dihydrate, USP | 0.45 |
| Hydrochloric Acid, NF or | |
| Sodium Hydroxide, NF for pH adjustment | 5–8 |
| Purified Water, USP | QS |

The solubility data for Brimonidine tartrate in the formulation vehicles are presented in Table II. The results show that the solubility of Brimonidine tartrate is highly pH-dependent and spans more than two orders of magnitude over the pH range of 5–8. The solubility decreases sharply as the pH increases. The results for the treated and untreated controls are very close, suggesting that centrifugation and filtration does not cause any significant loss of Brimonidine tartrate. The two solubility profiles obtained on consecutive days agree with each other.

TABLE II

| Solubility of Brimonidine tartrate in the Ophthalmic Solution Over pH Range of 5 to 8. | | | | |
|---|---|---|---|---|
| | STUDY 1 | | STUDY 2 | |
| Sample | pH$^a$ | Solubility$^e$ | pH$^a$ | Solubility$^e$ |
| 1 | 5.55 | ≧1644$^b$ | 5.50 | ≧200.6$^b$ |
| 2 | 5.92 | 132.6 | 5.92 | 160.8 |
| 3 | 6.14 | 30.4 | 6.06 | 50.1 |
| 4 | 6.57 | 7.55 | 6.90 | 3.19 |
| 5 | 7.00 | 2.69 | 7.40 | 1.19 |
| 6 | 7.45 | 1.17 | 7.77 | 0.63 |
| 7 | 7.83 | 0.62 | 7.86 | 0.58 |
| 8 | — | — | 7.88 | 0.54 |
| Control / (untreated) | — | 0.486$^c$ | — | — |
| Control / (treated) | — | 0.484$^d$ | — | — |

$^a$Measured after stirring for two-days before sample withdrawal for centrifugation and filtration.
$^b$Represents theoretical concentration based on sample weight. The sample solution was clear indicating that all of the Brimonidine tartrate had dissolved.
$^c$Concentration of Brimonidine tartrate in control before centrifugation and filtration step.
$^d$Concentration of Brimonidine tartrate in control after centrifugation and filtration step.
$^e$% w/v.

EXAMPLE 2

The pH-solubility profiles of Brimonidine tartrate in compositions (solutions) containing SECs and oxy-chloro components were determined. Particularly, the effects of sodium carboxymethylcellulose (CMC), an SEC, on the solubility of Brimonidine tartrate at various pH conditions were determined. The various concentrations of CMC tested with Brimonidine tartrate were 0%, 0.056%, 0.17%, 0.5%, 1.5% (w/v), Table III.

The samples tested also contained isotonic components, buffer components, and stabilized chlorine dioxide (Purite™), Table III. Sodium carboxymethyl-cellulose, sodium chloride, potassium chloride, calcium chloride dihydrate, and magnesium chloride hexahydrate were USP grade. Boric acid and sodium borate decahydrate were NF grade.

TABLE III

| | Sample 1 | Sample 2 | Sample 3 | Sample 4 | Sample 5 | |
|---|---|---|---|---|---|---|
| Brimonidine tartrate | 0.2% | 0.2% | 0.2% | 0.2% | 0.2% | (w/v) |
| CMC | 0.0% | 0.056% | 0.17% | 0.5% | 1.5% | (w/v) |
| Stabilized chlorine dioxide[a] | 0.005% | 0.005% | 0.005% | 0.005% | 0.005% | (w/v) |
| Sodium chloride | 0.58% | 0.58% | 0.58% | 0.58% | 0.58% | (w/v) |
| Potassium chloride | 0.14% | 0.14% | 0.14% | 0.14% | 0.14% | (w/v) |
| Calcium chloride, dihydrate | 0.02% | 0.02% | 0.02% | 0.02% | 0.02% | (w/v) |
| magnesium chloride, hexahydrate | 0.006% | 0.006% | 0.006% | 0.006% | 0.006% | (w/v) |
| boric acid | 0.2% | 0.2% | 0.2% | 0.2% | 0.2% | (w/v) |
| sodium tetraborate, decahydrate | 0.14% | 0.14% | 0.14% | 0.14% | 0.14% | (w/v) |

[a]Sold under the trademark Purite ™ by Allergan, Inc.

Each sample (1 through 5) was subjected to a range of pH's from about 7 to about 10. The vials containing the sample solutions were placed on a laboratory rotator and left for equilibration for fifteen days at room temperature (~21° C.). The sample solutions were filtered using a 25 mm diameter polysulfone cellulose acetate syringe type filter with 0.45 μm pore size. The filtered solutions were assayed for Brimonidine.

Conventional HPLC and detection techniques were used to detect and determine the concentrations of soluble Brimonidine tartrate. Table IV. The solubility is plotted against pH for each CMC concentration. The experimental data points were fitted to a modified Henderson-Hasselbalch equation using a nonlinear least squares routine (Deltagraph version 4.0 DeltaPoint, Inc.), FIG. 1. The $R^2$ values show the goodness of fit between the experimental values and the theoretical equation to be better than 0.991.

TABLE IV

| | Solubility of Brimonidine tartrate (%) | | | | |
|---|---|---|---|---|---|
| pH | 0% CMC | 0.056% CMC | 0.17% CMC | 0.5% CMC | 1.5% CMC |
| 6.67 | | 0.9302 | | 1.4464 | |
| 6.68 | 1.4256 | | 1.4200 | | |
| 6.93 | | | 0.7302 | | |
| 7.10 | | | | 0.3693 | |
| 7.11 | 0.2064 | 0.2828 | | | |
| 7.35 | | | | | 0.1904 |
| 7.56 | | | | 0.1451 | |
| 7.68 | 0.0786 | | | | |
| 7.77 | | 0.0721 | | | |
| 7.81 | | | 0.0735 | | |
| 8.10 | | | | | 0.0498 |
| 8.46 | | | | 0.0313 | |
| 8.50 | 0.0286 | | | | |
| 8.55 | | | 0.0328 | | |
| 8.67 | | | | | 0.0311 |
| 9.93 | | 0.0234 | | | |
| 9.94 | | | | 0.0250 | |
| 10.05 | | | 0.0241 | | |
| 10.09 | 0.0218 | | | | |
| 10.11 | | | | | 0.0222 |

FIG. 1 clearly shows that the solubility of Brimonidine tartrate tends to increase with increasing CMC concentrations. For example, at pH 7.5, the sample with 0% CMC resulted in 1000 ppm of Brimonidine tartrate; 0.056% CMC, 1300 ppm; 0.17% CMC, 1300 ppm; and 0.5%, 1600 ppm. At pH 7.5, the sample with 1.5% CMC resulted in about 1400 ppm, which is less than that of a similar solution with CMC at 0.5%. It is unclear at this point what the cause of this observation may be. Nonetheless, Brimonidine tartrate is more soluble in solution with a 1.5% CMC than with no CMC.

CMC is also effective to solubilize Brimonidine tartrate in a biological environment, for example the biological environment of the cornea.

EXAMPLE 3

Brimonidine Tartrate Dimers.

Brimonidine tartrate is added to a test tube containing a composition including chlorite. The test tube was allowed to equilibrate for ten days. Samples obtained from the test tube is analyzed. It is observed that a portion of the Brimonidine tartrate monomer units conjugated to form dimers.

While this invention has been described with respect to various specific examples and embodiments, it is to be understood that the invention is not limited thereto and that it can be variously practiced with the scope of the following claims.

What is claimed is:

1. A therapeutically effective aqueous ophthalmic composition comprising:
    up to about 0.15% (w/v) of 5-bromo-6-(2-imidozolin-2-ylamino) quinoxaline tartrate, the composition having a pH of about 7.0 or greater, and the 5-bromo-6-(2-imidozolin-2-ylamino) quinoxaline tartrate being soluble in the composition at about 21° C.

2. The composition of claim 1 which includes up to 0.15% (w/v) of 5-bromo-6-(2-imidozolin-2-ylamino)quinoxaline tartrate.

3. The composition of claim 1 which includes about 0.15% (w/v) of 5-bromo-6-(2-imidozolin-2-ylamino) quinoxaline tartrate.

4. The composition of claim 1 which includes 0.15% (w/v) of 5-bromo-6-(2-imidozolin-2-ylamino)quinoxaline tartrate.

5. The composition of claim 1 having a pH of 7.0 or greater.

6. The composition of claim 1 which further comprises a preservative selected from the group consisting of an oxychloro component and a quaternary ammonium compound in an amount effective to at least assist in preserving the composition.

7. The composition of claim 6 wherein the oxy-chloro component comprises a chlorite component.

8. The composition of claim 1 which is substantially free of anionic cellulosic derivatives.

9. The composition of claim 1 which is substantially free of carboxymethyl cellulose.

10. A therapeutically effective aqueous ophthalmic composition comprising:

up to about 0.15% (w/v) of a component selected from the group consisting of 5-bromo-6-(2-imidozolin-2-ylamino) quinoxaline, salts of 5-bromo-6-(2-imidozolin-2-ylamino) quinoxaline, esters of 5-bromo-6-(2-imidozolin-2-ylamino) quinoxaline and mixtures thereof, the composition having a pH of about 7.0 or greater, and the component being soluble in the composition at about 21° C.

11. The composition of claim 10 which includes up to 0.15% (w/v) of the component.

12. The composition of claim 10 which includes about 0.15% (w/v) of the component.

13. The composition of claim 10 which includes 0.15% (w/v) of the component.

14. The composition of claim 10 having a pH of 7.0 or greater.

15. The composition of claim 10, which further comprises an oxy-chloro component in an amount effective to at least assist in preserving the composition.

16. The composition of claim 15 wherein the oxy-chloro component comprises a chlorite component.

17. The composition of claim 10 which is substantially free of anionic cellulosic derivatives.

18. The composition of claim 10 which is substantially free of carboxymethyl cellulose.

19. The composition of claim 6 in which the preservative comprises benzalkonium chloride.

20. The composition of claim 10 which further comprises a preservative selected from the group consisting of an oxy-chloro component and a quaternary ammonium compound in an amount effective to at least assist in preserving the composition.

21. The composition of claim 20 in which the preservative comprises benzalkonium chloride.

22. The composition of claim 20 in, which the preservative comprises a oxy-chloro component.

* * * * *

UNITED STATES PATENT AND TRADEMARK OFFICE
CERTIFICATE OF CORRECTION

PATENT NO. : 6,641,834 B2
DATED : November 4, 2003
INVENTOR(S) : Olejnik et al.

It is certified that error appears in the above-identified patent and that said Letters Patent is hereby corrected as shown below:

<u>Column 10,</u>
Line 10, delete "Purite T" and insert in place thereof -- Purite™ --

Signed and Sealed this

Twentieth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,641,834 B2
DATED : November 4, 2003
INVENTOR(S) : Olejnik et al.

It is certified that error appears in the above-identified patent and that said Letters Patent is hereby corrected as shown below:

Column 3,
Line 48, delete "Bromodidine" and insert in place thereof -- Brimonidine --

Column 5,
Line 61, delete "disclose" and insert in place thereof -- disclosed --

Signed and Sealed this

Twenty-fourth Day of February, 2004

JON W. DUDAS
*Acting Director of the United States Patent and Trademark Office*

Disclaimer 6,641,834 — Orest Olejnik, Coto de Coza, CA (US); Edward D. S. Kerslake, Charlestown, MA (US). COMPOSITIONS CONTAINING ALPHA-2-ADRENERGIC AGONIST COMPONENTS. Patent dated November 4, 2003. Disclaimer filed August 25, 2004, by the assignee, Allergan, Inc.

The term of this patent, subsequent to the term of patent numbers, 6,627,210, 6,562,873 and 6,673,337 has been disclaimed.

*(Official Gazette, November 2, 2004)*

UNITED STATES PATENT AND TRADEMARK OFFICE
CERTIFICATE OF CORRECTION

PATENT NO. : 6,641,834 B2
DATED : November 4, 2003
INVENTOR(S) : Olejnik et al.

It is certified that error appears in the above-identified patent and that said Letters Patent is hereby corrected as shown below:

<u>Title page,</u>
Item [60], Related U.S. Application Data, delete "Jul. 14, 2002" and insert in place thereof -- Jul. 14, 2000 --

Signed and Sealed this

Twenty-first Day of December, 2004

JON W. DUDAS
*Director of the United States Patent and Trademark Office*